US 6,663,609 B2

(12) United States Patent
Williamson et al.

(10) Patent No.: US 6,663,609 B2
(45) Date of Patent: Dec. 16, 2003

(54) IMPLANTABLE PUMP CATHETER ACCESS PORT DENIAL DEVICE

(75) Inventors: Shobha Devi Williamson, Minneapolis, MN (US); Chris C. Christiansen, Oakdale, MN (US); Laura Sue McWilliam, Farmington Hills, MI (US)

(73) Assignee: Medtronic, Inc., Minneapolis, MN (US)

( * ) Notice: Subject to any disclaimer, the term of this patent is extended or adjusted under 35 U.S.C. 154(b) by 73 days.

(21) Appl. No.: 10/014,634

(22) Filed: Oct. 22, 2001

(65) Prior Publication Data

US 2003/0078550 A1 Apr. 24, 2003

(51) Int. Cl.[7] ............................................. A61M 31/00
(52) U.S. Cl. ............................. 604/288.01; 604/93.01; 604/175; 604/500; 128/12
(58) Field of Search ....................... 604/93.01, 115–117, 604/175, 149, 131–133, 141, 140, 151, 256, 288.01–288.04, 890.1, 891.1, 500, 502, 506; 128/DIG. 12

(56) References Cited

U.S. PATENT DOCUMENTS

| | | | | |
|---|---|---|---|---|
| 4,193,397 A | * | 3/1980 | Tucker et al. | 604/502 |
| 4,482,346 A | * | 11/1984 | Reinicke | 604/152 |
| 4,487,603 A | * | 12/1984 | Harris | 604/152 |
| 4,525,165 A | * | 6/1985 | Fischell | 604/131 |
| 4,544,371 A | * | 10/1985 | Dormandy et al. | 604/891.1 |
| 4,573,994 A | * | 3/1986 | Fischell et al. | 604/891.1 |
| 4,697,622 A | * | 10/1987 | Swift et al. | 141/1 |
| 4,714,462 A | * | 12/1987 | DiDomenico | 604/67 |
| 4,904,241 A | * | 2/1990 | Bark | 604/288.02 |
| 5,257,971 A | * | 11/1993 | Lord et al. | 604/500 |
| 5,328,465 A | | 7/1994 | Kratoska et al. | |
| 5,527,307 A | * | 6/1996 | Srisathapat et al. | 604/892.1 |
| 5,840,063 A | * | 11/1998 | Flaherty | 604/93.01 |
| 6,293,922 B1 | | 9/2001 | Haase | |
| 6,537,268 B1 | * | 3/2003 | Gibson et al. | 604/891.1 |

OTHER PUBLICATIONS

Product Brochure, "SynchroMed® Infusion System", *Medtronic, Inc.* (1995).

* cited by examiner

*Primary Examiner*—Michael J. Hayes
*Assistant Examiner*—Cris Rodriguez
(74) *Attorney, Agent, or Firm*—John W. Albrecht; Eric R. Waldkoetter (57) ABSTRACT

A device and method configured for placement into the catheter access port to prevent insertion of a needle into the catheter access port. The device a prong to engage the housing and lock itself in the catheter access port, an annular surface having geometry complimentary to the catheter access port to seal the denial device, and a face configured to deny needle access to the catheter access port. The device is also self sealing to substantial prevent deposition between itself and the catheter access port, is configured to be inserted without the need for tools, and is manufactured from biocompatible material. The method for inserting this device consists of aligning the device with the catheter access port, inserting the device, confirming it is in place, and sealing it into the catheter access port.

8 Claims, 13 Drawing Sheets

IMPLANTABLE PUMP CATHETER ACCESS PORT DENIAL DEVICE

FIELD OF THE INVENTION

This invention relates to medical devices and more particularly to an implantable drug pump.

BACKGROUND OF THE INVENTION

The medical device industry produces a wide variety of electronic and mechanical devices for treating patient medical conditions such as pacemakers, defribulators, neurostimulators, and therapeutic substance infusion devices. Medical devices can be configured to be surgically implanted or connected externally to the patient receiving treatment. Clinicians use medical devices alone or in combination with therapeutic substance therapies and surgery to treat patient medical conditions. For some medical conditions, medical devices provide the best, and sometimes the only, therapy to restore an individual to a more healthful condition and a fuller life. Implantable therapeutic substance infusion devices can be used to treat conditions such as pain, spasticity, cancer, and a wide variety of other medical conditions.

An implantable therapeutic substance infusion device is implanted by a clinician into a patient at a location appropriate for the therapy that interferes as little as practicable with patient activity. Typically, an infusion catheter is connected to the drug pump outlet and implanted to infuse the drug, infusate or other therapeutic substance at a programmed infusion rate and predetermined location to treat the medical condition. Reliable and accurate operation of the drug pump is important because both inadequate and unintended therapeutic substance infusion can create patient complications. In electrically powered implantable infusion devices, the period the infusion device can be implanted is often limited by factors such as battery consumption, corrosive damage, and mechanical wear. The relative large size of some implantable drug pumps can limit locations where the device can be implanted in a patient. An example of an implantable infusion device is shown in Medtronic, Inc. "SynchroMed® Infusion System" Product Brochure (1995).

Many drug pumps are configured, so the pump can be replenished with drug through the septum of a refill port while the pump is implanted, so the period the pump can be implanted may not be limited by drug capacity. This is commonly done by injecting a hypodermic needle through the skin and into the septum thereby providing access to refill the reservoir. In such devices a catheter access port is often provided in addition to the refill port. The catheter access port is also accessible percutaneously by hypodermic needle. Its septum provides direct access to the catheter bypassing the pump and allows a bolus of drug or fluid medication to be administered directly into the body at the site of the catheter. The catheter access port can also be used as a diagnostic tool to troubleshoot the catheter or infusion problems. An example of an implantable drug pump having a catheter access port is shown in U.S. Pat. No. 6,293,922 "Apparatus And Method For Guiding And Limiting Access By Hypodermic Needles To Septum Of A Human Implantable Medical Treatment Device" by Haase (Sep. 25, 2001).

Although some clinicians view the catheter access port septum as desirable, some are uncomfortable with its presence. If a person refilling the reservoir incorrectly injects the drug into the catheter access port instead of the refill port, this results in the drug being administered directly to the body. This may potentially cause a fatal overdose of the drug or other serious problems.

Accordingly, a need exists for a device and method that denies injections of drug directly into the catheter access port.

BRIEF SUMMARY OF THE INVENTION

An implantable pump catheter access port denial device is a denial device configured for placement into the catheter access port to prevent insertion of a needle into the catheter access port. The implantable pump comprises housing, a drug reservoir, a metering device, and a catheter access port. The drug reservoir is coupled to the housing and has a reservoir outlet. This reservoir outlet is coupled to a metering device that has its own metered outlet. The catheter access port is fluidly coupled to the metered outlet and is configured for receiving a needle to infuse drug directly into a catheter.

DETAILED DESCRIPTION OF THE INVENTION

Figure 1:
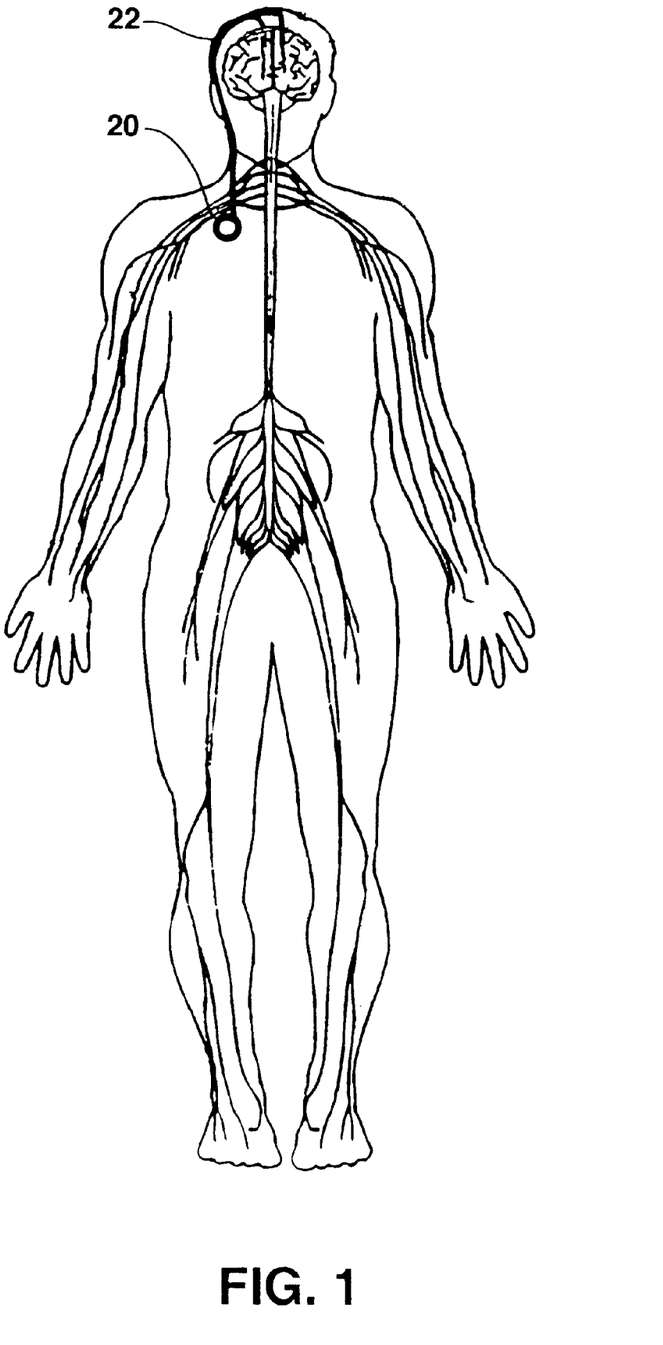
FIG. 1 shows a diagrammatic illustration of a portion of the nervous system of a human body in which an implantable drug pump and catheter have been implanted.

FIG. 1 shows the environment of an implantable medical device, 20, known as an implantable therapeutic substance infusion device, also known as a drug pump, having a neural embodiment. The therapeutic substance infusion device, 20, can be used for a wide variety of therapies to medical conditions (also known as medical indications) such as pain, spasticity, cancer, and many other medical conditions. The implantable therapeutic substance infusion device, 20, is typically implanted by a clinician such as a surgeon in a sterile surgical procedure performed under local, regional, or general anesthesia. Before implanting the therapeutic substance infusion device, a catheter, 22, is typically implanted with the distal end position at the desired therapeutic substance infusion site and the proximal end tunneled to the location where the therapeutic substance infusion device, 20, is to be implanted. The implantable therapeutic substance infusion device is generally implanted subcutaneously about 2.5 cm (1.0 inch) beneath the skin where there is sufficient subcutaneous tissue to support the implanted system. Once the therapeutic substance infusion device is subcutaneously implanted into the patient, the incision can be sutured closed and the therapeutic substance infusion device, 20, can begin operation.

The therapeutic substance infusion device, 20, operates to infuse a therapeutic substance, 42, at a programmed rate into a patient. The therapeutic substance, 42, is a product or substance intended to have a therapeutic effect such as pharmaceutical compositions, genetic materials, biologics, and other substances. Pharmaceutical compositions are chemical formulations intended to have a therapeutic effect such as intrathecal antispasmodics (e.g., balcofen), pain medications, chemotherapeutic agents, and the like. Pharmaceutical compositions are often configured to function in an implanted environment with characteristics such as stability at body temperature to retain therapeutic qualities, concentration to reduce the frequency of replenishment, and the like. Genetic materials are substances intended to have a direct or indirect genetic therapeutic effect such as genetic vectors, genetic regulator elements, genetic structural elements, DNA, and the like. Biologics are substances that are living matter or derived from living matter intended to have a therapeutic effect such as stem cells, platelets, hormones, biologically produced chemicals, and the like. Other substances, 42, are intended to have a therapeutic effect yet are not easily classified such as saline solution, fluoroscopy agents, and the like.

The therapeutic substance, 42, can be replenished in some embodiments of the implanted therapeutic substance infusion device, 20, by inserting a non-coring needle, 40, connected to a syringe filled with therapeutic substance, 42, through the patient's skin into a refill port, 28, on the therapeutic substance infusion device, 20. This can be accomplished by using the Medtronic Refill Kit, 8851. Also, therapeutic substance bolus can be administered by a clinician in some embodiment by inserting a non-coring needle, 40, connected to a syringe into a catheter access port, 30. This can be accomplished by using Medtronic CAP Kit, 8840. Typically, a clinician would administer a bolus for diagnostic purposes. If the therapeutic substance infusion device, 20, requires replacement due to conditions such as battery depletion or other condition, an incision is made near the implanted therapeutic substance infusion device, 20, and the old therapeutic substance infusion device is removed, also known as explanted. After the old therapeutic substance infusion device, 20, has been explanted, typically a new therapeutic substance infusion device, 20, is then implanted.

Figure 2A:
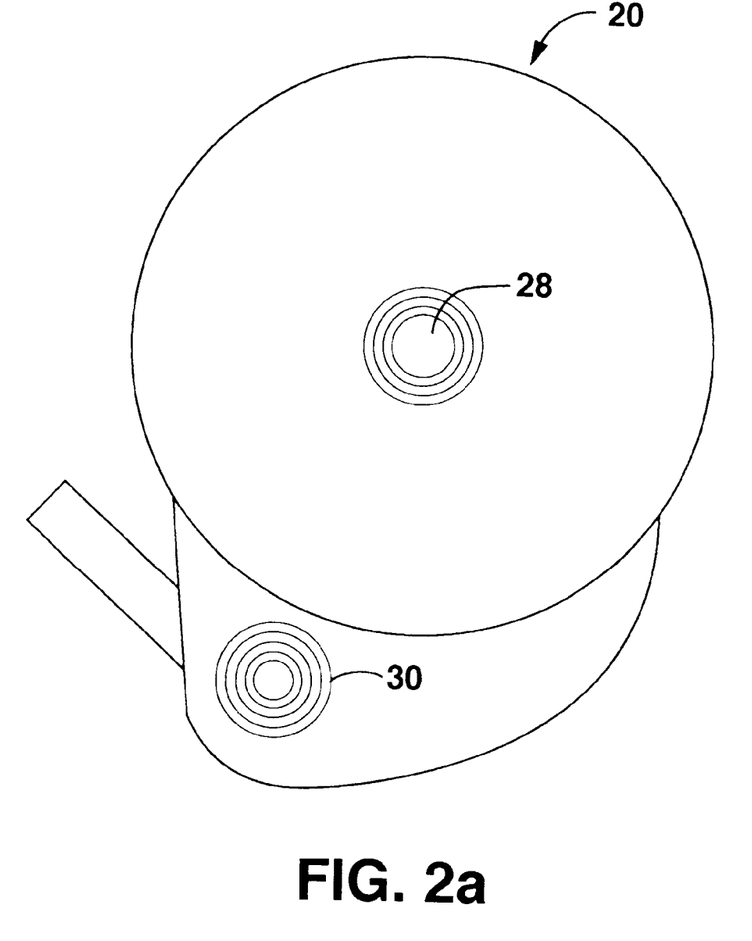
FIGS. 2a–2c show the top and side view of a schematic illustration of an implantable drug pump having catheter access port embodiments, as well as a fluid pathway schematic illustration.
Figure 2B:
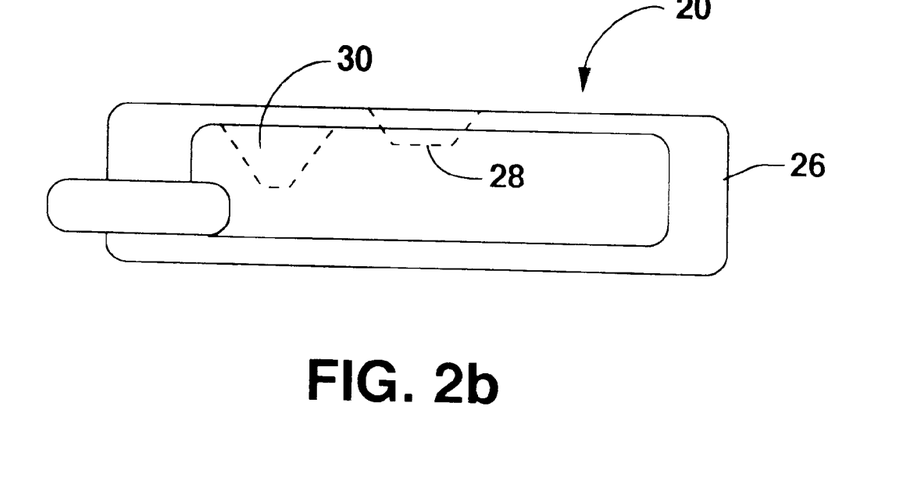
Figure 2C:
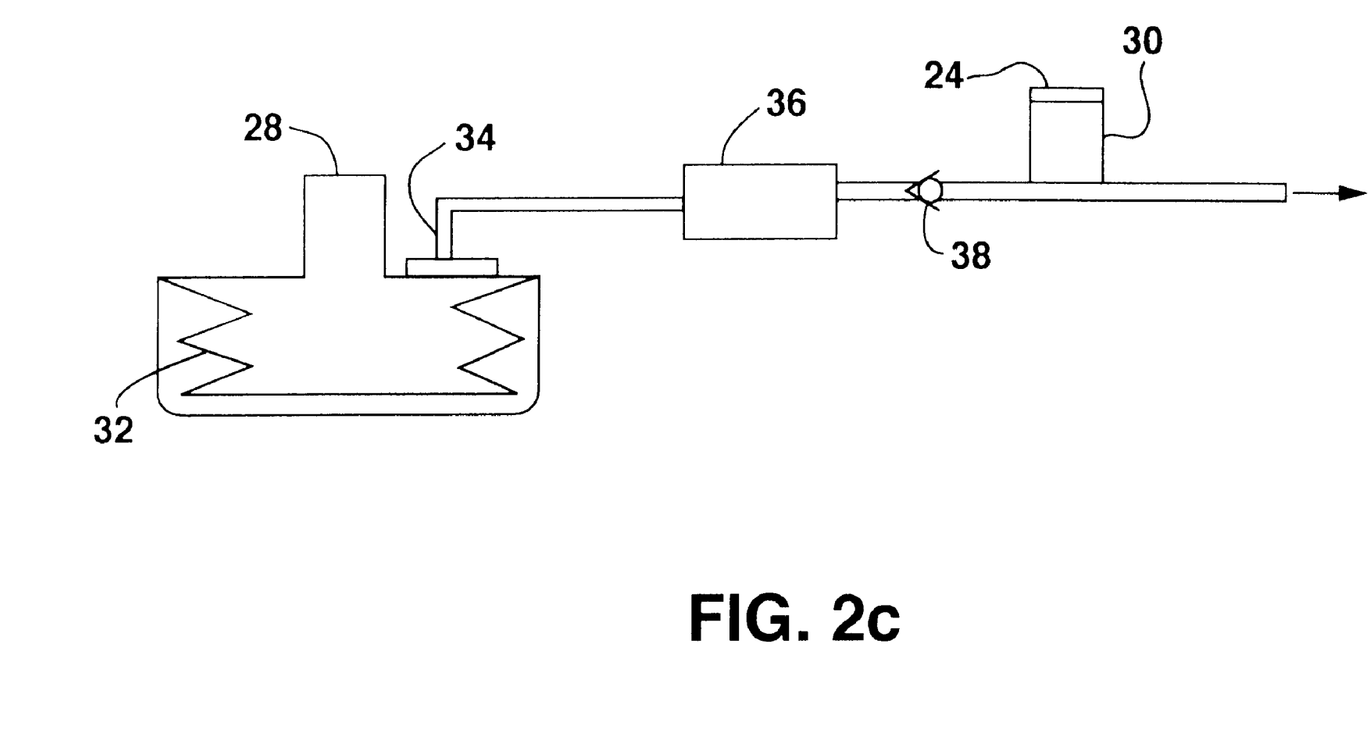
Figure 3:
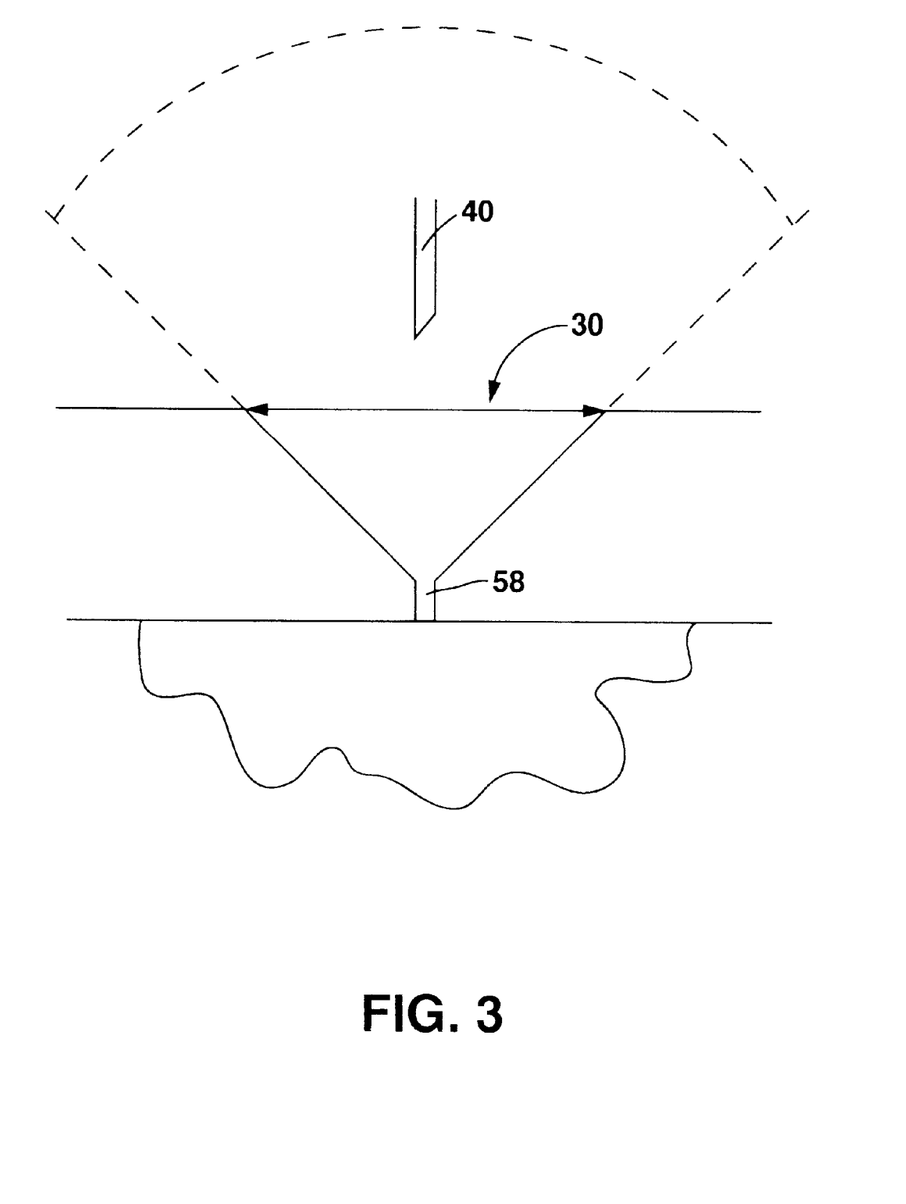
FIG. 3 shows an example of a catheter access port embodiment.
Figure 4A:
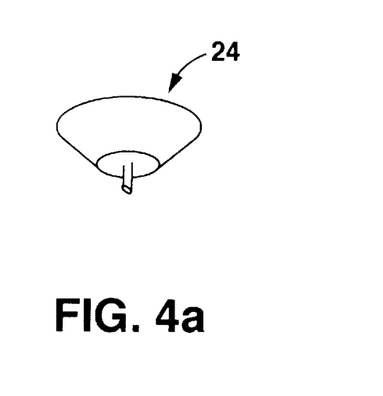
FIGS. 4a–4d show an embodiment of a catheter access port denial device that is self-retaining via a snap fit.
Figure 4B:
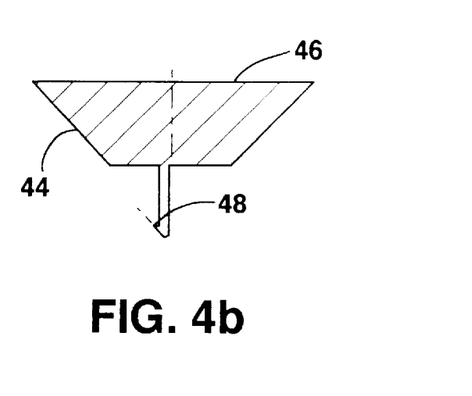
Figure 4C:
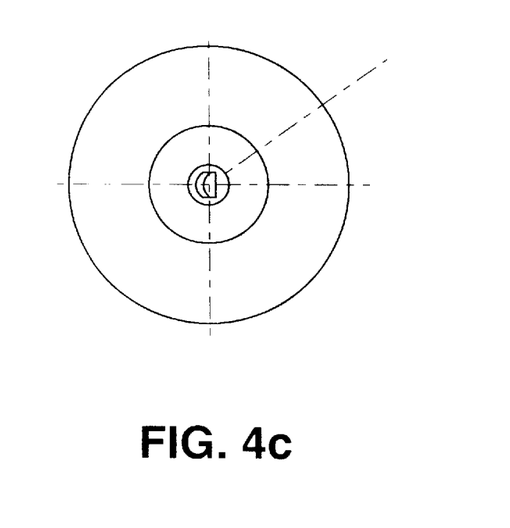
Figure 4D:
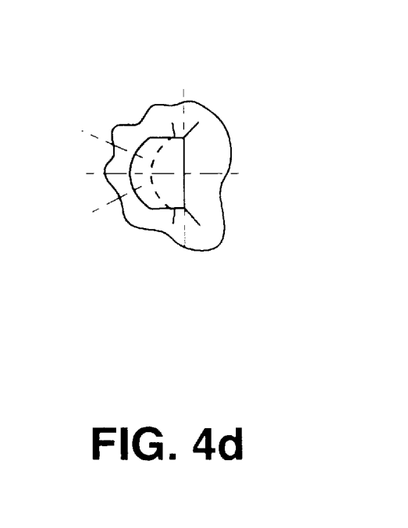

FIGS. 2a–2c show a top and side view of a schematic illustration of an implantable drug pump, 20, having catheter access port embodiments, 30, as well as a fluid pathway schematic illustration. FIG. 3 shows an example of a catheter access port embodiment, 30. Referring to these figures, in some embodiments of the implantable pump, 20, there are two ports by which therapeutic substance can be replenished. One is the refill port, 28, where therapeutic substance, 42, must pass through a drug reservoir, 32, and metering device, 36, before reaching the catheter, 22. The other is the catheter access port, 30, through which therapeutic substance, 42, can be sent directly into the catheter, 22. If a person refilling the reservoir incorrectly injects the drug, 42, into the catheter access port, 30, instead of the refill port, 28, this results in the drug, 42, being administered directly to the body, which can cause complications.

Accordingly, the catheter access port denial device, 24, and method, 50, 52, 54, 56, prevent injections of drug directly, 42, into the catheter access port, 30. The implantable pump catheter access port denial device, 24, is configured for placement into the catheter access port, 30, FIG. 3. The catheter access port, 30, is configured for receiving a needle, 40, to infuse drug directly, 42, into a catheter, 22.

FIGS. 4a–7j show various embodiments of the denial device, 24. The denial device, 24, is comprised of an annular surface, 44, a face, 46, and a prong, 48. The annular surface, 44, has a geometry that closely matches that of the catheter access port, 30. This aids in self-sealing as well as considerably impeding fibrotic growth. In addition, some embodiments comprise of a solid body surrounded by a gasket, which provides another form of sealing. The face, 46, of the denial device, 24, is configured to deny needle, 40, access to the catheter access port, 30, by providing a solid obstacle. The denial device, 24, as a whole is manufactured from a material that is biocompatible, such as polysulphone, titanium, and the like.

Figure 5A:
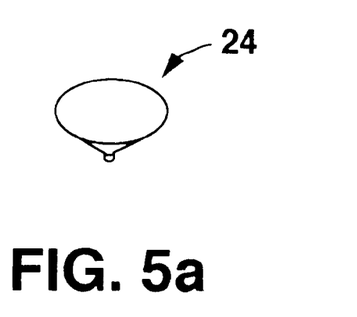
FIGS. 5a–5c show an embodiment of a catheter access port denial device that is self-retaining via a press fit.
Figure 5B:
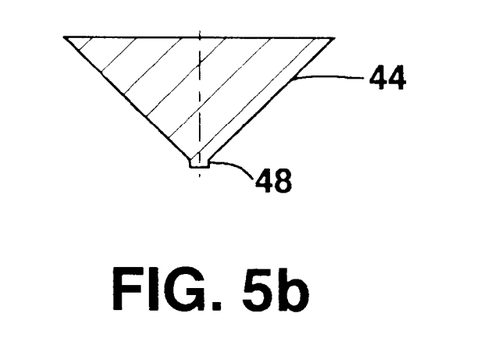
Figure 5C:
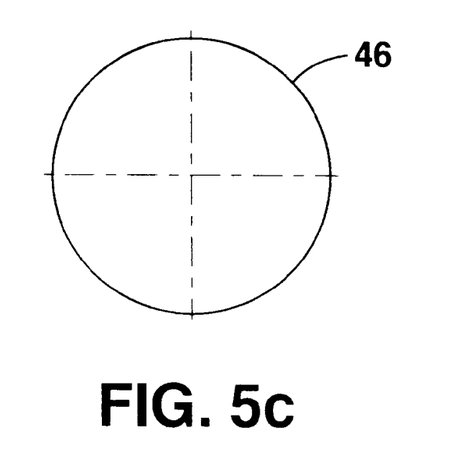
Figure 6A:
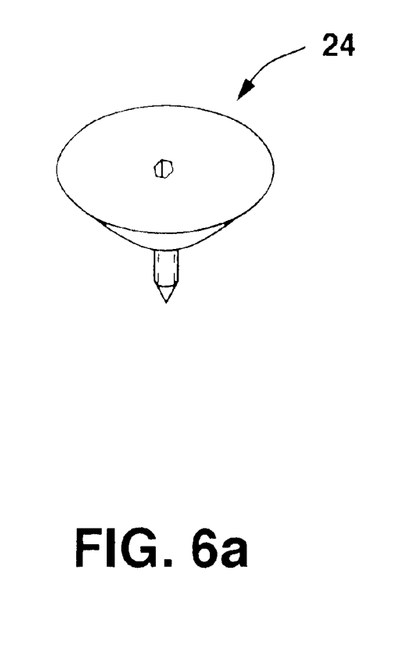
FIGS. 6a–6e show embodiments of a catheter access port denial device that is self-retaining via screw threads.
Figure 6B:
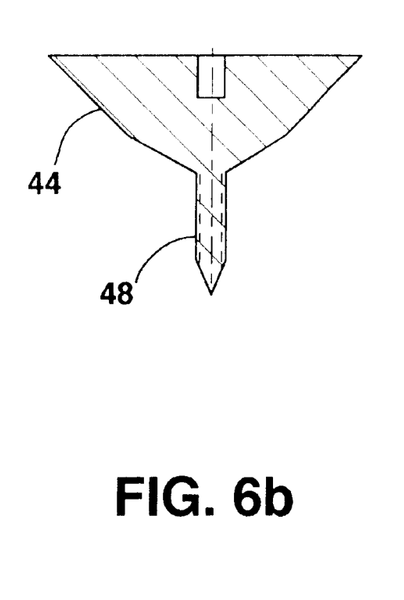
Figure 6C:
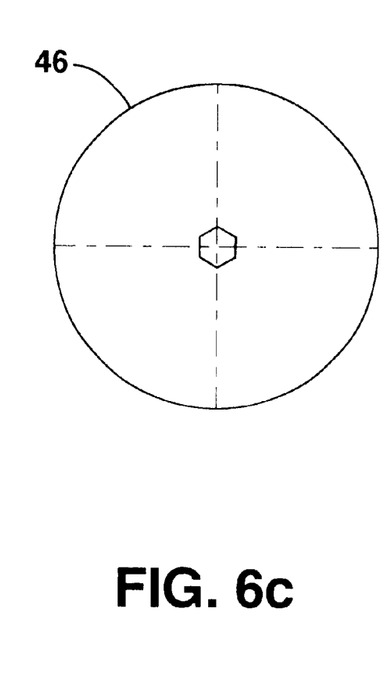
Figure 6D:
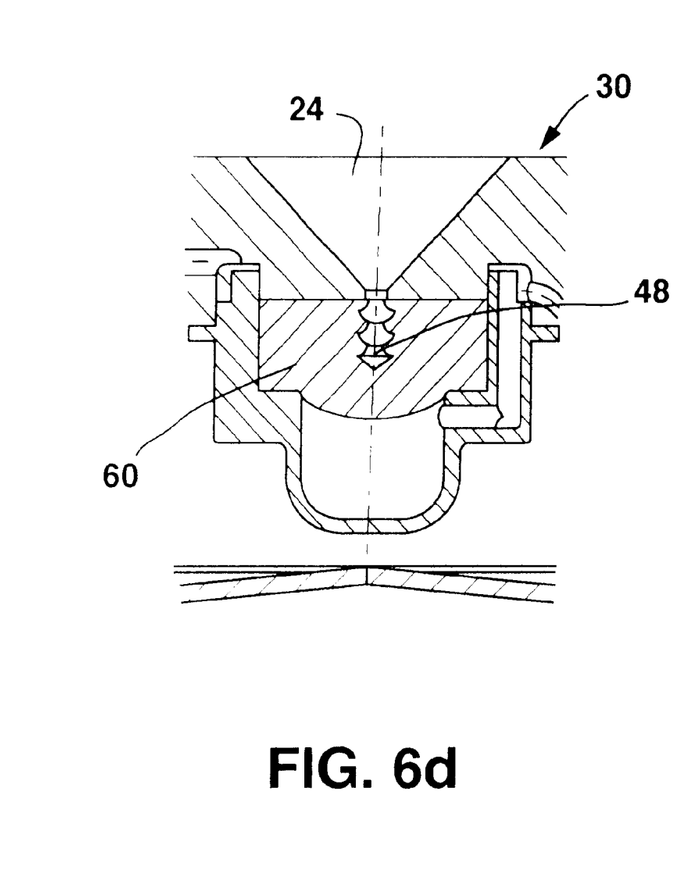
Figure 6E:
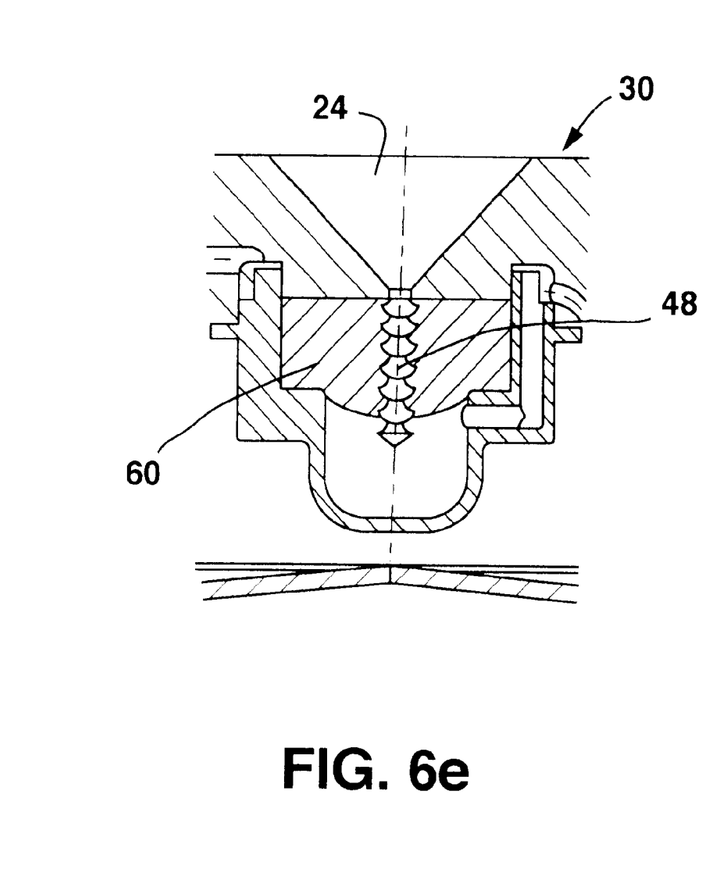

The prong, 48, of the denial device, 24, is configured to engage a catheter access port, 30, to lock the denial device, 24, in the catheter access port, 30. For example, FIGS. 4a–4d show a snap-fit embodiment. The prong, 48, of this embodiment is the snap-fit that extends through the needle entry, 58, to engage the underside of the catheter access port, 30. FIGS. 5a–5c show a press fit embodiment. The prong, 48, of a press fit embodiment typically engages the full length of the needle entry, 58, in order to provide a maximum length of interference. FIGS. 6a–6e show a screw embodiment. The prong, 48, of a screw embodiment consists of the threads that engage the denial device, 24, to the catheter access port, 30, and either partially or fully penetrate the septum, 60, beneath. In some cases, the prong, 48, is not an extension of the device, 24, but simply what engages it to the catheter access port, 30. For example, the epoxy used to adhere the device, 24, to the catheter access port, 30, would be considered the device's prong, 48.

Most embodiments of the denial device, 24, are configured to be inserted into the catheter access port, 30, without the need for tools. Examples of insertion without tools include a snap-fit design, FIGS. 4a–4d, and a press fit design, FIGS. 5a–5c. The press fit design is configured to be placed with the tightest interference tolerance that can be pressed by hand. All embodiments have characteristics to confirm that the device, 24, is in place. This ranges from the tactile assurance of the release of tension when the snap-fit embodiment is in place, to visual inspection that the face, 46, of the denial device, 24, is flush with the lowest section of the upper surface of the catheter access port, 24, that is coupled to the housing, 26.

The denial device, 24, is also self-retaining in the catheter access port, 30. FIGS. 4a–4d show an embodiment that is self-retaining via a snap fit beneath the needle entry, 58, section of the housing, 26. FIGS. 5a–5c show self-retaining via an interference fit between the prong, 48, and needle entry, 58, section of the housing, 26. FIGS. 6a–6e show an embodiment of self-retaining via screw threads engaging the underside of the catheter access port, 30, whether partially or fully through the underlying septum, 60.

Figure 7A:
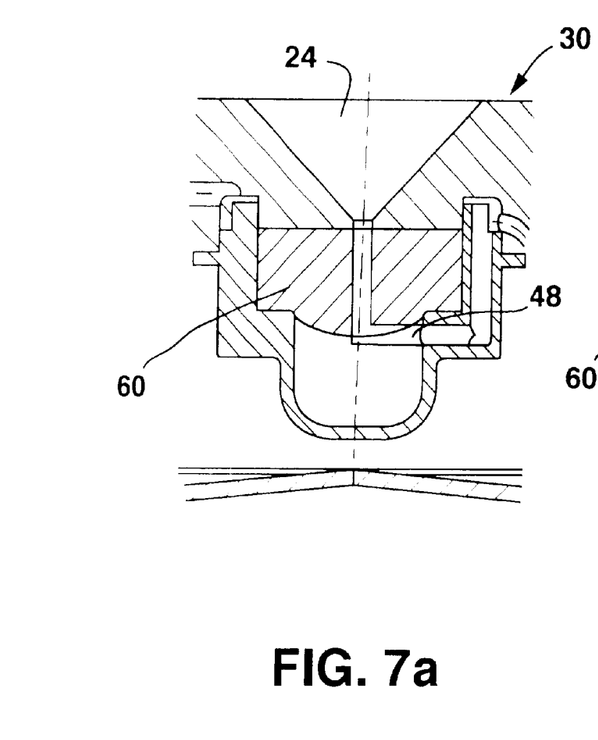
FIGS. 7a–7j show several embodiments of a catheter access port denial device in an implantable pump catheter access port, and, FIG. 8 shows a flowchart for a method for inserting a denial device in an implantable pump catheter access port.
Figures 7B, 7C:
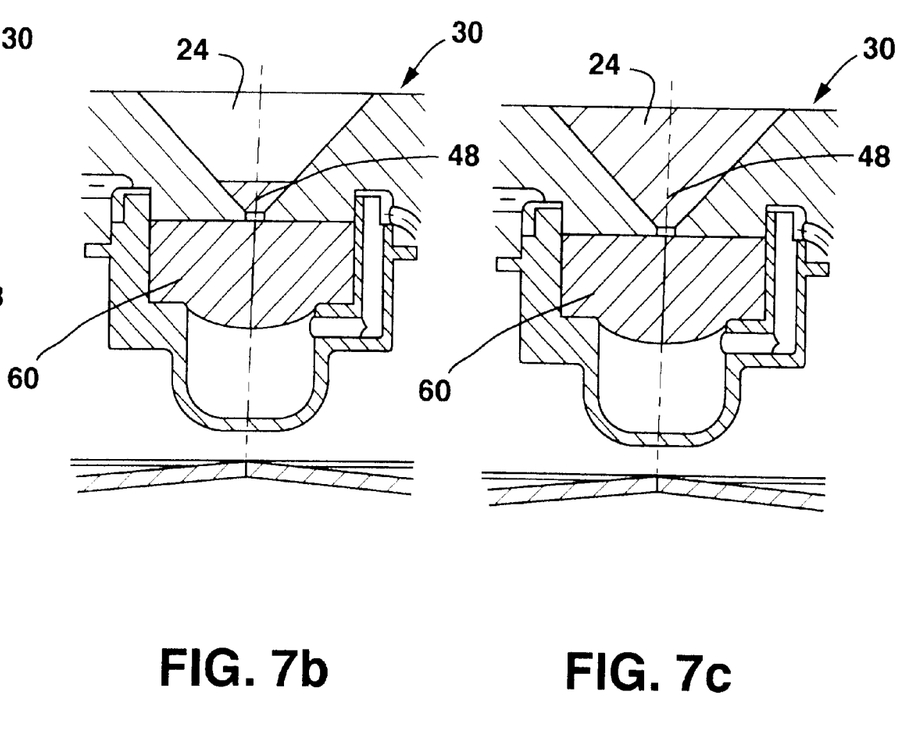
Figure 7D:
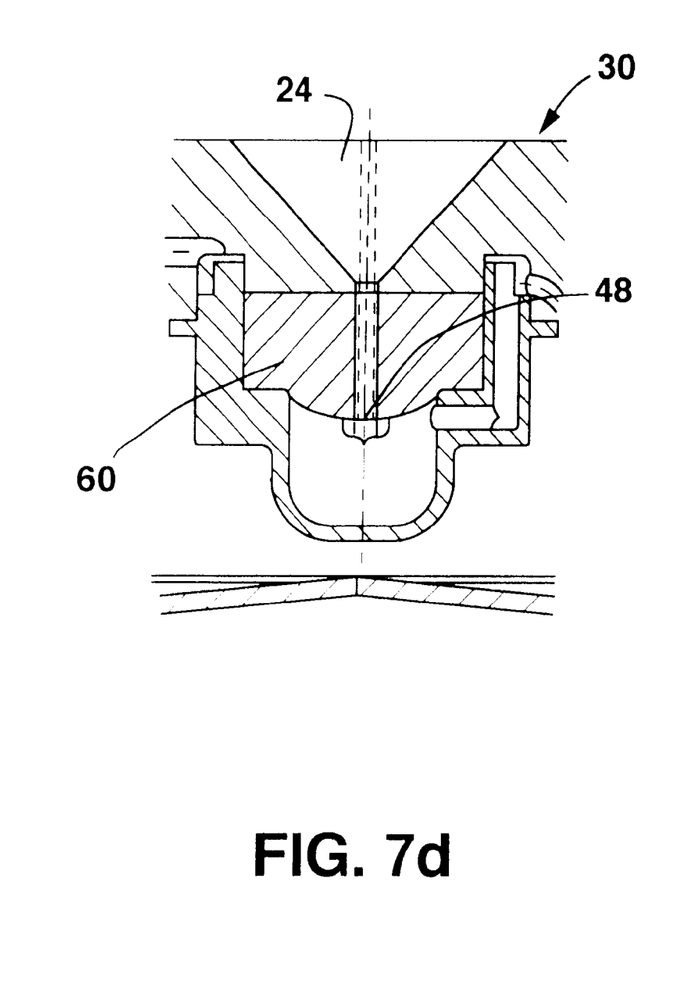
Figure 7E:
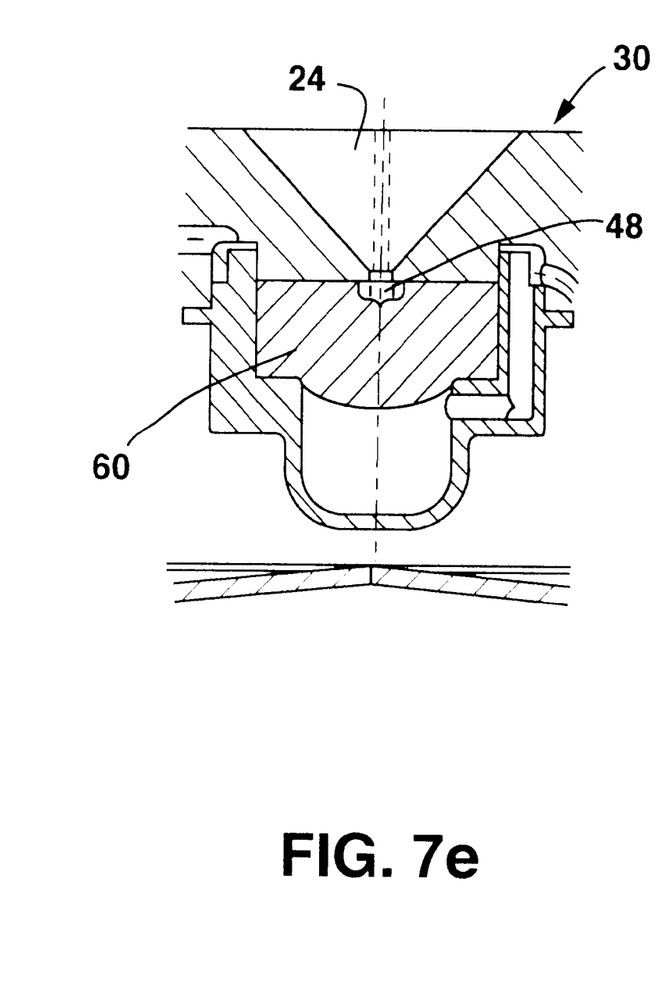
Figure 7F:
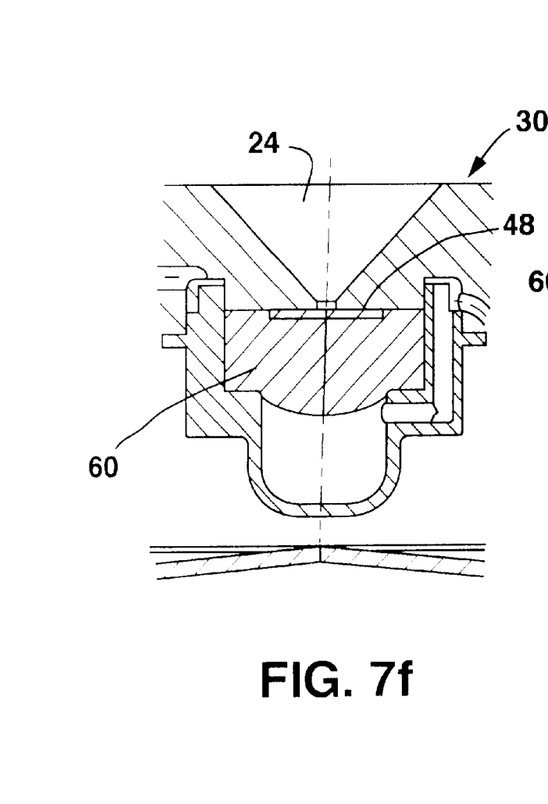
Figure 7G:
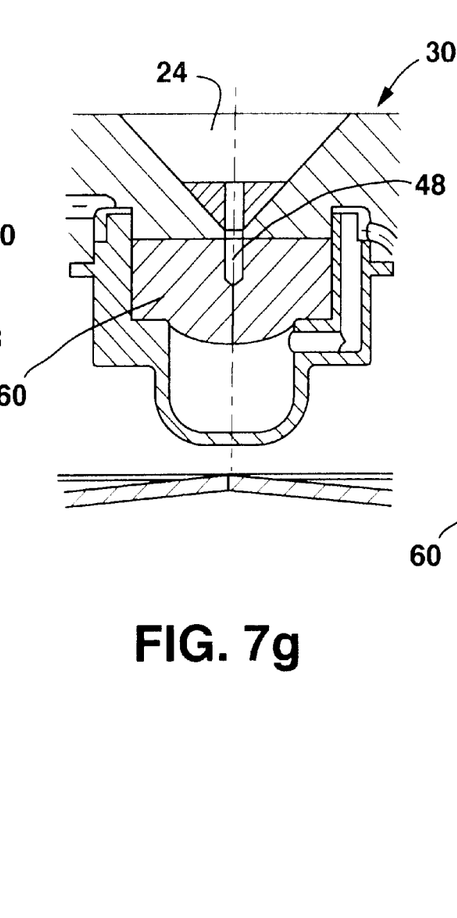
Figure 7H:
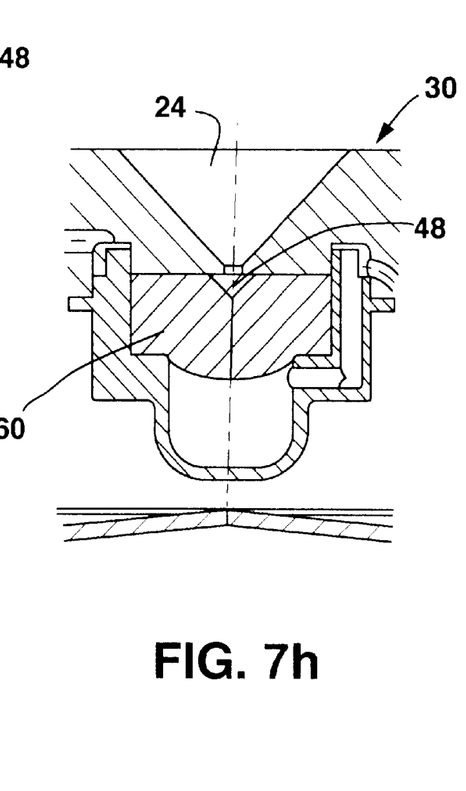
Figure 7I:
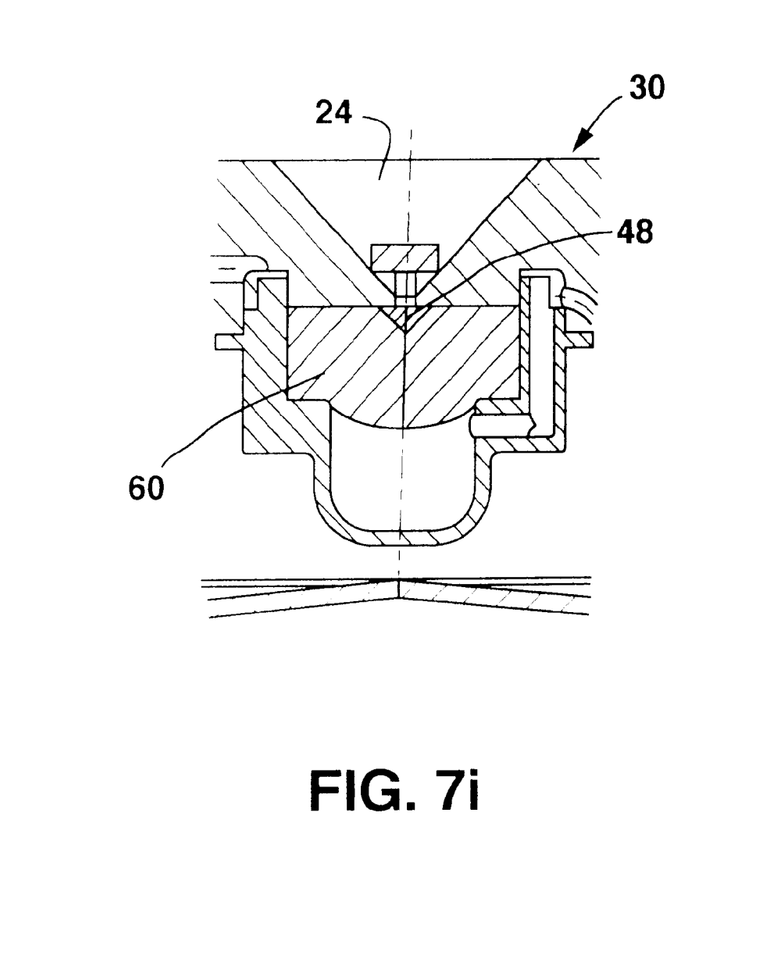
Figure 7J:
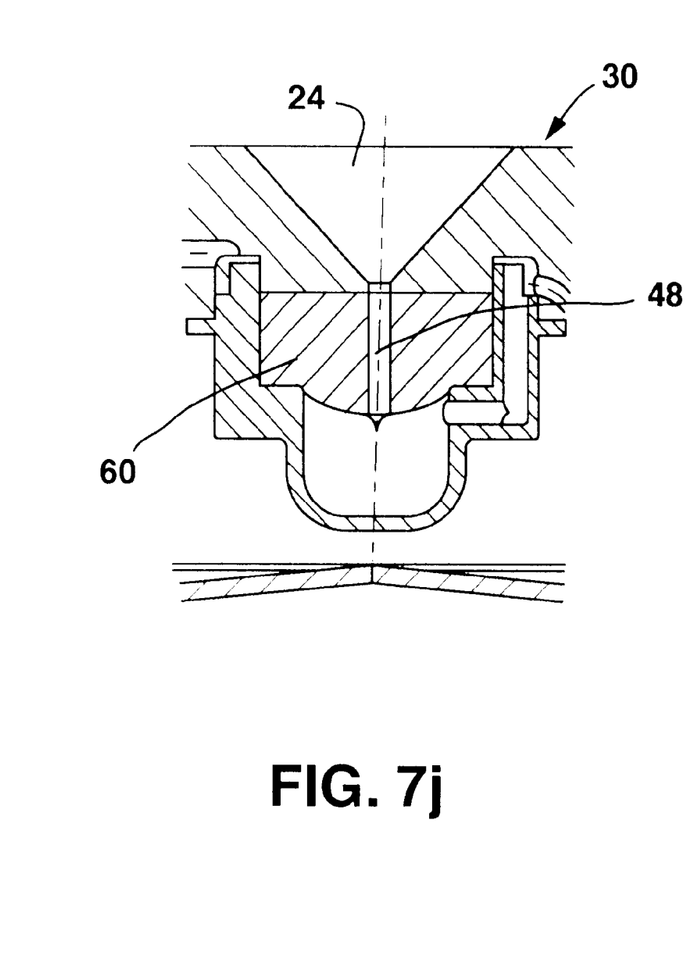

FIGS. 7a–7j shows several other geometries as well as various manners of self-retaining including epoxy and blind rivets. For example, FIG. 7a shows an embodiment with a prong, 48, that pierces the septum, 60, and anchors into a passage. An o-ring can be used to seal the hole. FIG. 7b shows a version of the press-fit design that also utilizes the tensile and shear strength of adhesive. FIG. 7c shows the denial device, 24, as an epoxy seal to the entrance. This manner is noninvasive to the needle entry, 58, section of the catheter access port, 30. FIGS. 7d–7e show the prong, 48, as a blind rivet that either partially or fully pierces the septum, 60. Once again, an o-ring can be used to seal the hole made in the septum, 60. FIG. 7f shows a denial device, 24, with a prong, 48, in the form of bars that fan outward to anchor the device to the housing. FIG. 7g takes the press fit design and uses its prong, 48, to pierce the septum, 60, for additional anchoring. Epoxy could be used in conjunction with this design to complete the seal. FIG. 7h utilizes a prong, 48, that is similar to an umbrella. The umbrella section folds out upon release past the needle entry, 58, and anchors to the housing, 26. The sides are robust enough to fold in and out, and sharp enough to cut through the septum, 60, without damaging the housing, 26. FIG. 7i takes advantage of the same idea while using a cuff to hold in the section of the prong, 48, that folds in and out. FIG. 7j also utilizes this idea by fully piercing the underlying septum, 60, while using an o-ring to seal the hole and possibly act as a cuff to hold the prong, 48, in.

Figure 8:
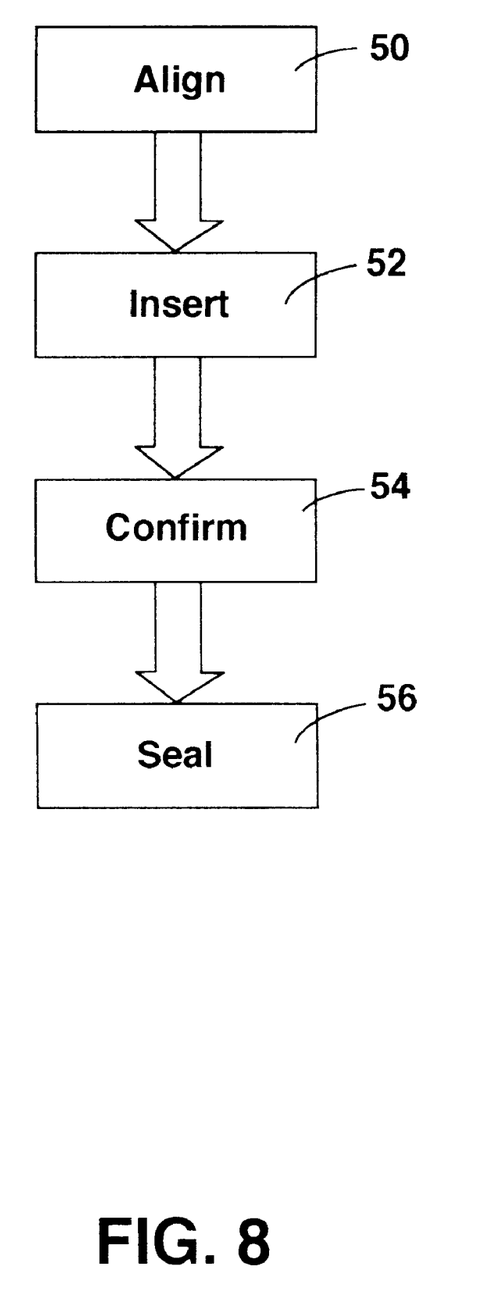

Referencing FIG. 8, a method for inserting a denial device, 24, in an implantable pump catheter access port, 30, comprises of alignment, 50, insertion, 52, confirmation, 54, and sealing, 56. The denial device, 24, can be aligned with a catheter access port, 30, by visually centering the prong, 48, with the needle entry, 58. This can be a rough estimate as the denial device, 24, is capable of guiding itself into place. The next step is inserting, 52, the device, 24, into the catheter access port, 30. This can be done by pressing, adhering, screwing, etc. the device, 24. After insertion, 52, is confirming, 54, that the denial device, 24, is in place. Insertion, 52, may be confirmed on most embodiments by visually checking that the face, 46, of the denial device, 24, is flush with the lowest part of the catheter access port, 30, that blends into the housing, 26. Other ways of confirmation, 54, are specific to the embodiment. For example, the embodiment illustrated in FIG. 4. Here, confirmation, 54, may be established by perceiving the movement of the snap fit into place. Next is sealing, 56. This step is accomplished once the denial device, 24, has been confirmed in place. Examples of sealing, 56, include the presence of gaskets and epoxy.

What is claimed is:

1. An implantable pump comprising:

a housing;

a drug reservoir coupled to the housing, the drug reservoir having a reservoir outlet;

a metering device coupled to the reservoir outlet, the metering device having a metered outlet;

a catheter access port fluidly coupled to the metered outlet, the catheter access port configured for receiving a needle to infuse drug directly into a catheter; and, a denial device configured for placement into the catheter access port to prevent insertion of a needle into the catheter access port.

2. The implantable pump as in claim 1 wherein the denial device is self-retaining in the catheter access port.

3. The implantable pump as in claim 1 wherein the denial device is self-sealing to substantially prevent substance deposition between the denial device and the catheter access port.

4. The implantable pump as in claim 1 wherein the denial device is configured to be inserted into the catheter access port without the need for tools.

5. The implantable pump as in claim 1 wherein the denial device is manufactured from a material that is biocompatible.

6. An implantable pump comprising:

a housing;

a drug reservoir coupled to the housing, the drug reservoir having a reservoir outlet;

a metering device coupled to the reservoir outlet, the metering device having a metered a catheter access port fluidly coupled to the metered outlet, the catheter access port configured for receiving a needle to infuse drug directly into a catheter and, a means for denial configured for placement into the catheter access port to prevent insertion of a needle into the catheter access port.

7. A denial device for an implantable pump catheter access port, comprising:

a prong configured to engage a catheter access port to lock the denial device in the catheter access port;

an annular surface having a geometry complimentary to the catheter access port to seal the denial device; and, a face configured to deny needle access to the catheter access port.

8. A method for inserting a denial device in an implantable pump catheter access port, comprising:

aligning a denial device with a catheter access port;

inserting the denial device into the catheter access port;

confirming the denial device has been fully inserted into the catheter access port; and, sealing the denial device in the catheter access port.

* * * * *

UNITED STATES PATENT AND TRADEMARK OFFICE
CERTIFICATE OF CORRECTION

PATENT NO. : 6,663,609 B2
DATED : December 16, 2003
INVENTOR(S) : Williamson et al.

It is certified that error appears in the above-identified patent and that said Letters Patent is hereby corrected as shown below:

Column 5,
Line 36, insert -- catheter access port denial device, -- between "pump" and "comprising".

Column 6,
Line 16, insert -- catheter access port denial device, -- between "pump" and "comprising".
Line 21, insert -- outlet -- after "metered".
Line 24, insert -- ; -- between "catheter" and "and".

Signed and Sealed this

Twenty-second Day of November, 2005

JON W. DUDAS
*Director of the United States Patent and Trademark Office*